United States Patent
Nagase

(10) Patent No.: US 7,238,805 B2
(45) Date of Patent: Jul. 3, 2007

(54) PROCESS FOR PREPARING TRIAZINE COMPOUNDS

(75) Inventor: Hisato Nagase, Shizuoka-ken (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 11/449,613

(22) Filed: Jun. 9, 2006

(65) Prior Publication Data

US 2006/0281919 A1     Dec. 14, 2006

(30) Foreign Application Priority Data

Jun. 9, 2005   (JP) ............................. 2005-169994

(51) Int. Cl.
  *C07D 251/70*   (2006.01)
(52) U.S. Cl. ..................... 544/197; 544/198
(58) Field of Classification Search ................ 544/197, 544/198

See application file for complete search history.

(56) References Cited

FOREIGN PATENT DOCUMENTS

JP           2004-161727 A      6/2004

OTHER PUBLICATIONS

JP2004-161727-Machine Translation, Nov. 26, 2006.*
E. Schaumann, "Methods of Organic Chemistry", 4th edition, vol. E9C, 1988, (Thieme Stuttgart), Chapters 2-3, pp. 667-796.

* cited by examiner

*Primary Examiner*—Venkataraman Balasubramanian
(74) *Attorney, Agent, or Firm*—Sughrue Mion, PLLC

(57) ABSTRACT

A process for preparing a triazine compound represented by formula (1) including reacting a 2,4,6-trichlorotriazine, in the presence of a base, with a compound represented by the formula (2) in an organic solvent containing water and an aromatic hydrocarbon is provided.

20 Claims, No Drawings

PROCESS FOR PREPARING TRIAZINE COMPOUNDS

CROSS-REFERENCE TO RELATED APPLICATION

This application claims priority under 35 USC 119 from Japanese Patent Application No. 2005-169994, the disclosure of which is incorporated by reference herein.

BACKGROUND OF THE INVENTION

1. Field of the Invention

The present invention relates to a process for preparing triazine compounds useful in applications such as additives for improving resistance to a plasticizer, the printability of thermosensitive recording materials, and the lubricity of mechanical friction sliding portions of various machinery, particularly under a high temperature environment; fluorescent whitening agents; or synthetic intermediates thereof.

2. Description of the Related Art

Syntheses of 2,4,6-triaminotriazine compounds have been studied for many years. In general, a variety of syntheses thereof have been reported (see, for example, E. SCHAUMANN, "Methods of Organic Chemistry" 4th edition, Volume E9C, 1988, (THIEME STUTTGART), Chapters 2–3, pp. 667–796).

These 2,4,6-triaminotriazine compounds are usually obtained by reacting 2,4,6-trichlorotriazine as a raw material with an amine. For example, a preparation using a methylethylketone, an ethyl acetate, or the like as an organic solvent has been disclosed (see, for example, Japanese Patent Application Laid-Open (JP-A) No. 2004-161727).

However, of three chloro groups on a triazine ring, while two chloro groups are respectively easily substituted with an amino group, the remaining substitution on the third chloro group may occur slowly depending on the kinds, reaction conditions, or the like of the amines used. As a result, a long time is required to complete the reaction. Further, when the reaction is slow, a disubstituted intermediate in which two amino groups are substituted remains. Accordingly, many problems in production exist such as the extra effort required to separate the remaining disubstituted intermediate.

SUMMARY OF THE INVENTION

In view of the above, the present invention has been devised in order to address problems in the existing art and provides a simple process for preparing triazine compounds, in particular, 2,4,6-triaminotriazine compounds. Further, the present invention provides a preparation process in which a reaction time is short, yield is high, and mass production with high purity is possible.

A first aspect of the present invention is a process for preparing a triazine compound represented by the following formula (1) which comprises reacting 2,4,6-trichlorotriazine, in the presence of a base, with a compound represented by the following formula (2) in a solvent including water and an aromatic hydrocarbon based organic solvent.

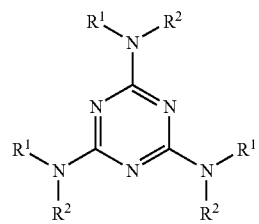

Formula (1)

$R^1R^2NH$  Formula (2)

wherein, $R^1$ represents an alkyl group, an aryl group or a heterocyclic group that may be substituted, and $R^2$ represents a hydrogen atom, or an alkyl group, an aryl group or a heterocyclic group that may be substituted.

A second aspect of the present invention is the process for preparing a triazine compound according to the first aspect, wherein in the formula (1), $R^1$ represents an alkyl group and $R^2$ represents a hydrogen atom or an alkyl group.

A third aspect of the present invention is the process for preparing a triazine compound according to the first or second aspects, wherein the aromatic hydrocarbon based organic solvent is toluene.

A fourth aspect of the present invention is the process for preparing a triazine compound according to any one of the first to third aspects, wherein an inorganic base is used as the base.

A fifth aspect of the present invention is the process for preparing a triazine compound according to the fourth aspect, wherein a sodium hydroxide, a potassium hydroxide or a combination thereof is used as the inorganic base.

A sixth aspect of the present invention is the process for preparing a triazine compound according to any one of the first to fifth aspects, wherein the base is used in an amount of an equimolar amount to an amount 10 times in molar ratio based on the 2,4,6-trichlorotriazine.

A seventh aspect of the present invention is the process for preparing a triazine compound according to the first aspect, wherein the base and water are added after adding the compound represented by the formula (2) to a mixture of 2,4,6-trichlorotriazine and the aromatic hydrocarbon based organic solvent.

An eighth aspect of the present invention is the process for preparing a triazine compound according to the first aspect, wherein after adding a part of the compound represented by the formula (2) to a mixture of 2,4,6-trichlorotriazine and the aromatic hydrocarbon based organic solvent in advance, the remaining compound represented by the formula (2) and the base are simultaneously added.

A ninth aspect of the present invention is the process for preparing a triazine compound according to the first aspect, wherein after adding the base and water to a mixture of 2,4,6-trichlorotriazine and the aromatic hydrocarbon based organic solvent, the compound represented by the formula (2) is added thereto.

A tenth aspect of the present invention is the process for preparing a triazine compound according to the first aspect, wherein to a mixture of 2,4,6-trichlorotriazine and the aromatic hydrocarbon based organic solvent, water is added and thereafter, the base and the compound represented by the formula (2) are added.

An eleventh aspect of the present invention is the process for preparing a triazine compound according to the first aspect, wherein HCl is neutralized by adding an excess of the compound represented by the formula (2).

A twelfth aspect of the present invention is the process for preparing a triazine compound according to any one of the seventh to tenth aspects, wherein an inorganic base is used as the base.

A thirteenth aspect of the present invention is the process for preparing a triazine compound according to any one of the seventh to tenth aspects, wherein the aromatic hydrocarbon based organic solvent is toluene.

DETAILED DESCRIPTION OF THE INVENTION

A process for preparing a triazine compound represented by formula (1) of the present invention comprises reacting 2,4,6-trichlorotriazine, in the presence of a base, with a compound represented by the following formula (2) in a solvent including water and an aromatic hydrocarbon based organic solvent.

Hereinafter, the triazine compound represented by the following formula (1) and the compound represented by the following formula (2) will be explained in detail. Formula (1)

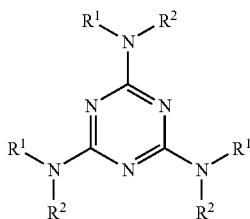

$R^1R^2NH$            Formula (2)

In the formulae, $R^1$ represents an alkyl group, aryl group or heterocyclic group that may be substituted, and $R^2$ represents a hydrogen atom, or an alkyl group, aryl group or heterocyclic group that may be substituted.

In the formulae, the alkyl group represented by $R^1$ and $R^2$ represents a linear or cyclic alkyl group, and is preferably an alkyl group having 1 to 30 carbon atoms, more preferably, an alkyl group having 1 to 25 carbon atoms, and still more preferably an alkyl group having 1 to 20 carbon atoms.

Examples of the alkyl group include methyl, ethyl, n-propyl, iso-propyl, n-butyl, iso-butyl, tert-butyl, n-hexyl, n-octyl, n-nonyl, iso-nonyl, tert-nonyl, cyclohexyl, decyl, dodecyl, tetradecyl, hexadecyl, octadecyl, 4-chlorobenzyl, (4-ethoxyphenyl)methyl, N,N-diethylcarbamoylmethyl, N,N-dibutylcarbamoylmetyl, 1-(N,N-dibutylcarbamoyl)ethyl, 2-methoxyethyloxy, and the like.

In the above formulae, the aryl group represented by $R^1$ and $R^2$ is preferably an aryl group having 6 to 30 carbon atoms, more preferably, an aryl group having 6 to 25 carbon atoms, and still more preferably, an aryl group having 6 to 20 carbon atoms. Examples of the aryl group include phenyl, naphthyl, anthracenyl, phenanthryl, pyrenyl, pherylenyl, and the like.

In the above formulae, the heterocyclic group represented by $R^1$ and $R^2$ may be a saturated heterocyclic ring or an unsaturated heterocyclic ring, and is preferably a 3 to 10 membered heterocyclic ring, more preferably, a 4 to 8 membered heterocyclic ring, and still more preferably, a 5 to 7 membered heterocyclic ring. Examples of the heterocyclic ring include an oxazole ring, thiazole ring, imidazole ring, pyrazole ring, triazole ring, isooxazole ring, isothiazole ring, furan ring, thiophen ring, pyrrol ring, pyridine ring, pyrimidine ring, triazine ring, and the like. However, in a product, a hetero atom does not bind to the amino group which is bound to the triazine ring. The heterocyclic group may be a benzo-condensed ring, or may have a substituent.

The groups represented by $R^1$ and $R^2$ may further have a substituent, and examples of the substituent include an alkyl group (that is the same as the alkyl group for $R^1$ and $R^2$, with the same preferred examples), an aryl group (that is the same as the aryl group for $R^1$ and $R^2$, with the same preferred examples), a heterocyclic group (that is the same as the heterocyclic group for $R^1$ and $R^2$, with the same preferred examples), an alkoxy group (preferably, an alkoxy group having the same alkyl group as $R^1$ and R2, where the alkyl group is the same as the alkyl group for $R^1$ and $R^2$, with the same preferred examples including methoxy, ethoxy, isopropoxy, decyloxy, dodecyloxy, tetradecyloxy, hexadecyloxy, octadecyloxyl, and the like), an aryloxy group (phenoxy and the like), a halogen (fluorine, chlorine, bromine, and the like), a cyano group, an alkylthio group, an arylthio group, an amino group, and the like.

In the formula (1), $R^1$ is preferably an alkyl group and $R^2$ is preferably a hydrogen atom or an alkyl group.

Hereinafter, specific examples of the compounds that can be prepared by the process of the present invention will be described, but the present invention is not limited thereto.

A-1

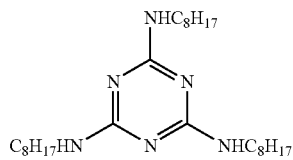

A-2

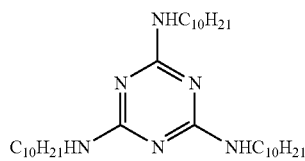

-continued
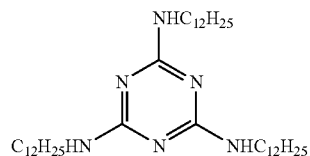
A-3
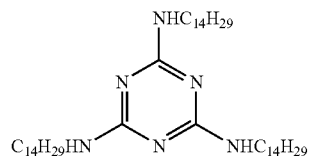
A-4
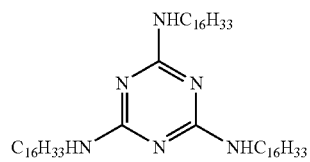
A-5
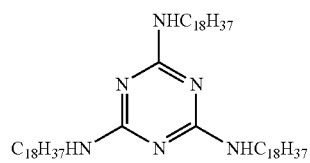
A-6
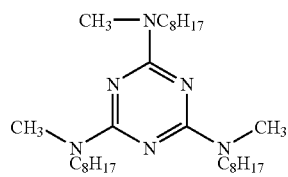
A-7
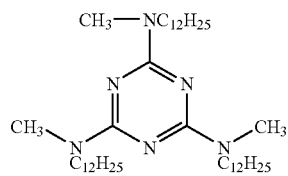
A-8
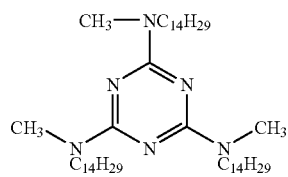
A-9
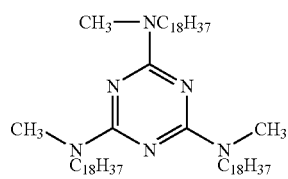
A-10
A-11

-continued
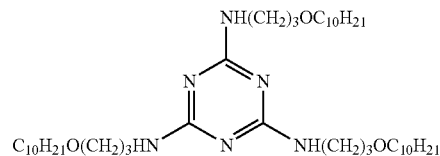
A-12
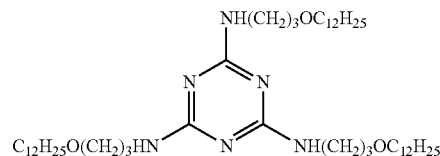
A-13
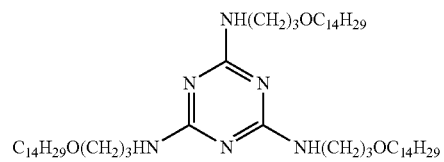
A-14
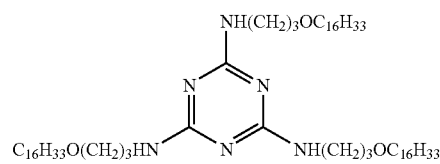
A-15
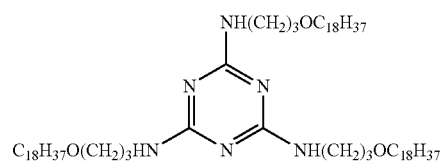
A-16
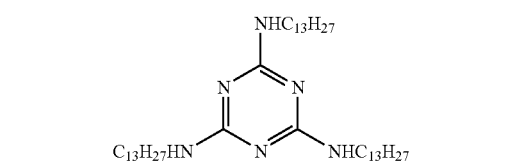
A-17
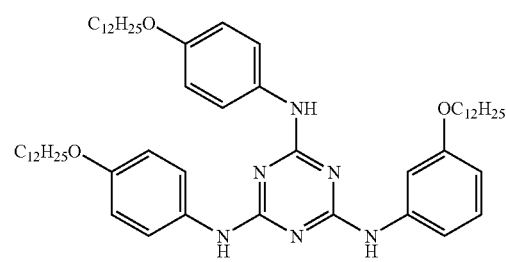
A-18

-continued
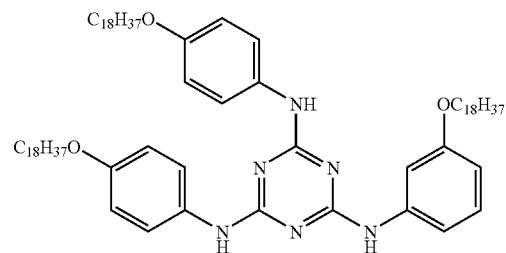
A-19
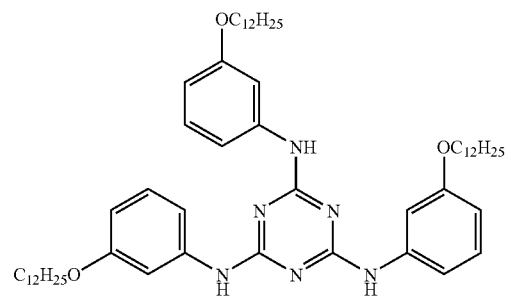
A-20
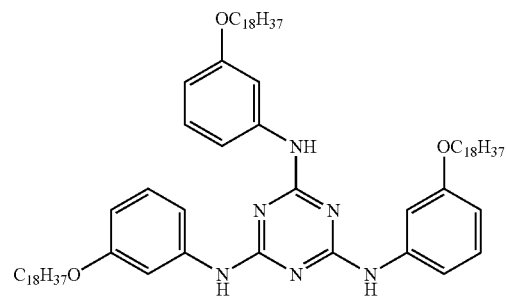
A-21
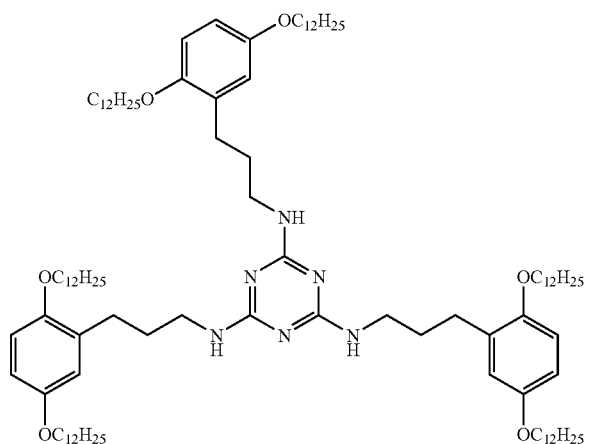
A-22

-continued
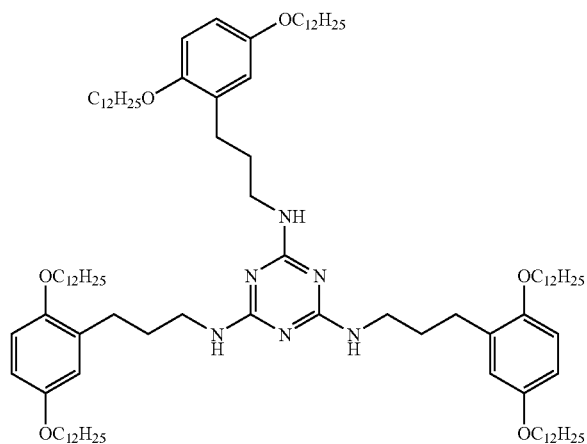
A-23
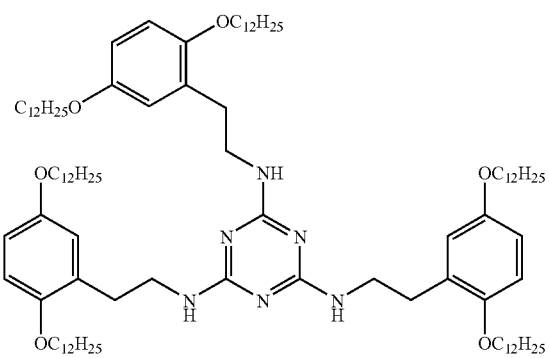
A-24
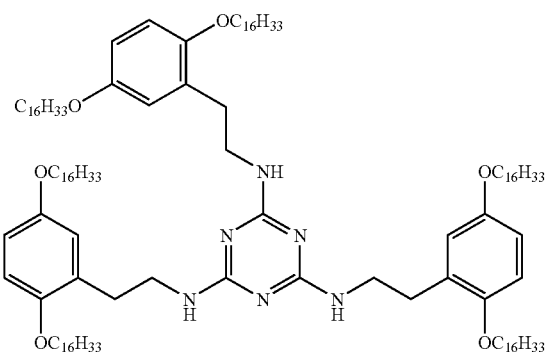
A-25
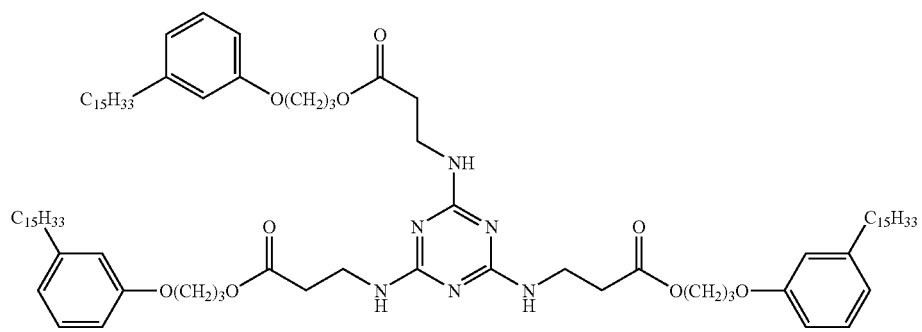
A-26

-continued

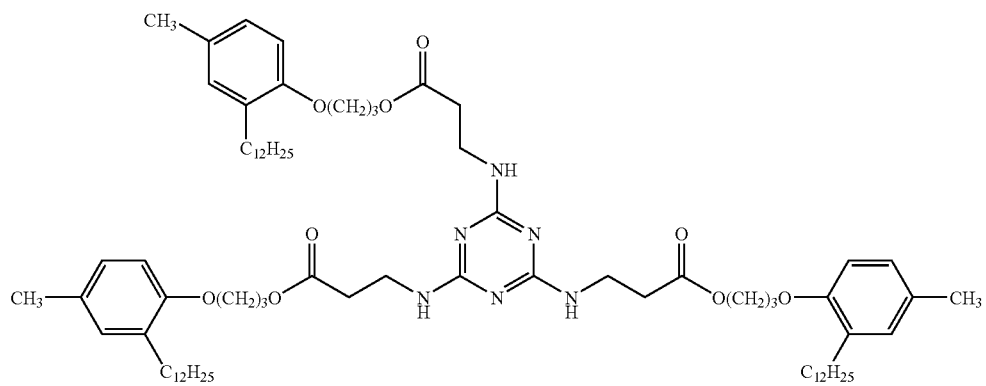

A-27

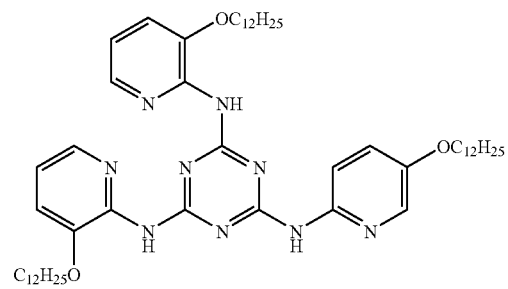

In the process for preparing a triazine compound of the present invention, the following conditions can be used.

The solvent to be used in the reaction is a mixed solvent (hereinafter, referred to as "the mixed solvent of the present invention") containing water and an aromatic hydrocarbon based organic solvent.

The aromatic hydrocarbon based organic solvent is not limited, and examples thereof include benzene, toluene, xylene, and the like. Among these, from the viewpoint of solubility of the substituted (monosubstituted or disubstituted) intermediates in which 2,4,6-triaminotriazine is substituted with an amine ($R^1R^2NH$), toluene, benzene, or the like are preferred, and toluene is particularly preferred. Still more preferably, a solvent containing water and toluene is used.

The mixing ratio of water and the aromatic hydrocarbon based organic solvent is preferably such that the amount (volume ratio) of water is equivalent to or less than, more preferably a half of or less than, the amount of aromatic hydrocarbon based organic solvent. The lower limit of the mixing ratio is not limited, and is about 1/30.

Further, the following solvents may be mixed with the mixed solvent of the present invention, if necessary, in view of improvement of solubility with respect to the substrate: nitrile solvents such as acetonitrile, propionitrile, and the like; ester solvents such as ethyl acetates, butyl acetates, and the like; ketone solvents such as acetone, methyl ethyl ketone, and the like; ether solvents such as diethyl ether, tetrahydrofuran, methyl-t-butylether, dioxane, and the like; amide solvents such as dimethyl formamide, dimethyl acetoamide, and the like; halogenated hydrocarbon solvents such as chloroform, methylene chloride, dichloroethane, chlorobenzene, and the like; other solvents such as sulfolane, dimethylsulfoxide, and the like; and combinations thereof.

The amount of other solvents to be added may be within a range that does not impair the effects of the present invention and is preferably 50% or less, and more preferably 25% or less, with respect to the mixed solvent.

The solvent in the present invention may be used in an amount such that the raw materials are dissolved, and can be selected appropriately depending on the raw materials used and the like. The amount of the solvent used preferably has as high a concentration as possible, from the viewpoint of reaction efficiency. However, when the solvent is used at a higher concentration, the viscosity increases and stirring efficiency is reduced. Further, when the solvent is used at a lower concentration, volumetric efficiency is reduced. Therefore, it is necessary to select the amount of the solvent used accordingly.

The preparation process of the present invention is a process for preparing 2,4,6-triaminotriazine compounds by reacting 2,4,6-trichlorotriazines with a compound represented by the formula (2).

It is thought that the preparation process of the present invention involves an initial reaction where one equivalent amount of 2,4,6-trichlorotriazine is reacted with one equivalent amount of the compound represented by the formula (2) to produce the monosubstituted intermediates, which are then reacted with a further one equivalent amount of the compound represented by the formula (2) to obtain a disubstituted intermediate. During the reaction until the disubstituted intermediate is produced, that is, at the time of reacting one equivalent of 2,4,6-trichlorotriazine with two equivalents of the compound represented by the formula (2), the temperature under which the reaction is conducted is preferably 0° C. to 70° C., more preferably 0° C. to 60° C., and still more preferably 0° C. to 50° C., for the purpose of increasing the selectivity of the reaction.

Further, the reaction temperature at the time of producing the compound (trisubstituted product) represented by the formula (1) from the disubstituted intermediate (or mono-substituted intermediates) is preferably 60° C.~180° C., and more preferably 65~150° C.

The amount of the compound represented by the formula (2) used in the present invention is preferably 2.5 times to 5 times, and more preferably 3 times to 4.5 times, with respect to the molar amount of 2,4,6-trichlorotriazine.

In the reaction, HCl is generated as the reaction proceeds, and it is, therefore, presumed that the resulting HCl reduces the reaction speed. In order to remove the HCl, the base is added.

In the initial stage of the reaction of two equivalents of the compound represented by the formula (2) with 2,4,6-trichlorotriazine, an inorganic base or an organic base can be used as the base, but the base used is not limited thereto.

Specific examples of the inorganic base include lithium hydroxide, sodium hydroxide, potassium hydroxide, cessium hydroxide, calcium hydroxide, carbonates (sodium carbonate, potassium carbonate, sodium hydrogen carbonate, potassium hydrogen carbonate, and the like), acetates (sodium acetate, potassium acetate, and the like), oxalates (sodium oxalate, sodium hydrogen oxalate, and the like), and the like. Among them, sodium hydroxide, potassium hydroxide, and potassium carbonate are preferred, and sodium hydroxide and potassium hydroxide are more preferred.

Further, preferable examples of the organic base include triethylamine, diisopropylethylamine, pyridine, picoline, ruthidine, N,N-dimethylaniline, and the like. Among these, from the viewpoints of production cost and environmental impact, or the like, inorganic bases are preferred.

The bases may be used alone or in combination of two or more thereof. The base is preferably used in an amount that is equimolar to 10 times in molar ratio, more preferably 1.5 to 5 times in molar ratio, and still more preferably 2 to 4 times in molar ratio with respect to the amount of 2,4,6-trichlorotriazine.

In the preparation of the present invention, mixing order and mixing method of 2,4,6-trichlorotriazine, with the compound represented by the formula (2), the base, water, the organic solvent, and the like are not limited, but the following methods (1) to (3) are mainly used:
(1) The compound of the formula (2) is added to a mixture of 2,4,6-trichlorotriazine and an aromatic hydrocarbon based organic solvent, and then a base and water are added thereto (method (1)).
(2) A part of the compound represented by the formula (2) is added to a mixture of 2,4,6-trichlorotriazine and an aromatic hydrocarbon based organic solvent in advance, and then, to the resulting mixture, the remaining compound represented by the formula (2) and a base are added simultaneously (method (2)).
(3) A base and water are added to a mixture of 2,4,6-trichlorotriazine and an aromatic hydrocarbon based organic solvent, and then, a compound of the formula (2) is added thereto (method (3)).

In addition to the methods above, a variety of methods such as a method where water is added to a mixture of 2,4,6-trichlorotriazine and an aromatic hydrocarbon based organic solvent, and then a base and a compound of the formula (2) are alternately added can be used. It is preferable to select an optimal method in accordance with the respective reaction systems.

Further, in the reaction, an excess of the compound represented by the formula (2) may be used in order to neutralize the HCl instead of the base. The methods (1) to (3) described above are preferred, and the method (1) is more preferred.

In the preparation process of the present invention, the reaction time is not limited, but is preferably 30 minutes to 24 hours, more preferably 60 minutes to 12 hours, and still more preferably 90 minutes to 10 hours. In the preparation process of the present invention, in order to optimize the reaction speed, reaction efficacy, or the like, a catalyst, salt, or the like may be added appropriately to the reaction system in addition to the base.

After completion of the reaction, isolation of the product can be carried out. The isolation methods are not particularly limited, and include a method in which a poor solvent is added to the reaction system to precipitate the product and the product is filtered and washed with water, a method in which after completion of the reaction, the water layer is removed from the reaction system to separate the aromatic hydrocarbon based organic solvent and the resulting solution is washed with water and the organic solvent is distilled off, a method in which after completion of the reaction, the water layer is removed and then, a poor solvent is added to the reaction system to precipitate the product and the product is filtered and washed with water, or a method in which after a product is extracted with an organic solvent such as an ethyl acetate, a diethyl ether, a chloroform, a methylene chloride, or the like and washed with water, the organic solvent is distilled off. Purification of the product obtained is not particularly limited, and conventional purifying methods such as recrystallization, column chromatography, distillation, or the like can be applied.

Hereinafter, the present invention will be described with reference to the following examples, but the present invention is not limited thereto.

EXAMPLES

Example 1

<Synthesis of the Exemplary Compound (A-1): Method (1)>

9.2 g of 2,4,6-trichlorotriazine was dissolved into 80 ml of toluene and the solution was cooled to an inner temperature of 10° C. To this solution, a solution of 21.3 g of n-octylamine in 20 ml of toluene was added dropwise such that the inner temperature was maintained at 30° C. or below and then, the resulting mixture was stirred for a further 30 minutes. Then, a solution of 6.6 g of sodium hydroxide in 10 ml of water was added and the mixture was heated for 1 hour at 40° C. Thereafter, the reaction mixture was heated to reflux for 8 hours. Disappearance of the disubstituted intermediate was confirmed by HPLC, and then, the product was cooled to 50° C., the water layer was removed, and an organic layer obtained was washed with water and dried with an anhydrous sodium sulfate. Toluene was distilled off at reduced pressure, and the residues obtained were recrystallized from a mixture of an ethyl acetate and a methanol to produce the exemplary compound (A-1) at a yield of 90%.

$^1$H-NMR(CDCl$_3$)δ; 4.60–4.82 (br, 3H), 3.25–3.41 (m, 6H), 1.56 (m, 6H), 1.20–1.40 (m, 30H), 0.86 (t, 9H) melting point: 50° C. MASS: $C_{27}H_{54}N_6$ Calcd: 462.44. Found: 462.4.

Example 2

<Synthesis of the Exemplary Compound (A-3): method (1)>922 g of 2,4,6-trichlorotriazine was dissolved into 8 L of toluene and the solution was cooled to an inner temperature of 18° C. To this solution, a solution of 3058 g of n-dodecylamine in 2 L of toluene was added dropwise such that the inner temperature was maintained at 30° C. or below and then, the resulting mixture was stirred for a further 60 minutes. Then, a solution of 715 g of sodium hydroxide in 3 L of water was added and the mixture was heated to reflux for 8 hours. Disappearance of the disubstituted intermediate was confirmed by HPLC, and then, the product was cooled to 60° C., the water layer was removed, and 30 L of methanol was poured to precipitate solids. The resulting solids were filtered, dried and recrystallized from an ethyl acetate to obtain the exemplary compound (A-3) at a yield of 94%. $^1$H-NMR, melting point and mass spectra data for the exemplary compound (A-3) will be showed below:

$^1$H-NMR(CDCl$_3$)δ; 4.62–4.80 (br, 3H), 3.25–3.41 (m, 6H), 1.56 (m, 6H), 1.20–1.44 (m, 54H), 0.87 (t, 9H) melting point: 82° C. MASS: C$_{39}$H$_{78}$N$_6$ Calcd: 630.63. Found: 630.6.

Example 3

<Synthesis of the Exemplary Compound (A-3): Method (2)>

9.2 g of 2,4,6-trichlorotriazine was dissolved into 80 ml of toluene and the solution was cooled to an inner temperature of 10° C. To this solution, a solution of 20.4 g of n-dodecylamine in 20 ml of toluene was added dropwise such that the inner temperature was maintained at 30° C. or below and then, the resulting mixture was stirred for a further 30 minutes. Then, a solution of 10.2 g of n-dodecylamine in 10 ml of toluene and a solution of 6.6 g of sodium hydroxide in 50 ml of water was added simultaneously. Thereafter, the reaction mixture was heated to reflux for 8 hours. Disappearance of the disubstituted intermediate was confirmed by HPLC, and then, the product was cooled to 50° C., the water layer was removed, and the residue was poured into 300 mL of methanol to precipitate solids. The solids obtained were filtered, dried and recrystallized from an ethyl acetate to produce the exemplary compound (A-3) at a yield of 92%. HPLC confirmed that the product obtained was the exemplary compound (A-3).

Example 4

<Synthesis of the Exemplary Compound (A-3): Method (3)>

9.2 g of 2,4,6-trichlorotriazine was dissolved into 80 ml of toluene, to which 6.6 g of sodium hydroxide and 50 ml of water were added, and the mixture was cooled to an inner temperature of 10° C. To this reaction mixture, a solution of 30.6 g of n-dodecylamine in 20 ml of toluene was added dropwise such that the inner temperature was maintained at 50° C. or below, and the mixture was further stirred for 30 minutes. Thereafter, the reaction mixture was heated to reflux for 8 hours. Disappearance of the disubstituted intermediate was confirmed by HPLC, and then, the product was cooled to 50° C., the water layer was removed, and the residue obtained was poured into 300 ml of methanol to precipitate the solids. The solids obtained were filtered, dried and recrystallized from an ethyl acetate to produce the exemplary compound (A-3) at a yield of 90%. HPLC confirmed that the product obtained was the exemplary compound (A-3).

Example 5

<Synthesis of the Exemplary Compound (A-6): Method (1)>

9.2 g of 2,4,6-trichlorotriazine was dissolved into 80 ml of toluene, to which a solution of 44.5 g of n-octadecylamine in 20 ml of toluene was added dropwise such that the inner temperature was maintained at 30° C. or below and then, the resulting mixture was stirred for a further 30 minutes. Then, a solution of 6.6 g of sodium hydroxide in 50 ml of water was added and the mixture was heated to reflux for 8 hours. Disappearance of the disubstituted intermediate was confirmed by HPLC, and then, the product was cooled to 70° C., the water layer was removed, and the residue obtained was poured into 300 ml of methanol to precipitate the solids. The solids obtained were filtered, dried and recrystallized from an ethyl acetate to produce the exemplary compound (A-6) at a yield of 95%. $^1$H-NMR, melting point and mass spectra data for the exemplary compound (A-6) will be showed below:

$^1$H-NMR(CDCl$_3$)δ; 4.60–4.82 (br, 3H), 3.25–3.41 (m, 6H), 1.56 (m, 6H), 1.20–1.48 (m, 90H), 0.86 (t, 9H) melting point: 94° C. MASS: C$_{57}$H$_{114}$N$_6$ Calcd: 882.91. Found: 882.9.

Example 6

<Synthesis of the Exemplary Compound (A-8): Method (1)>

9.2 g of 2,4,6-trichlorotriazine was dissolved into 80 ml of toluene, to which a solution of 32.9 g of n-dodecylmethylamine in 20 ml of toluene was added dropwise such that the inner temperature was maintained at 30° C. or below and then, the resulting mixture was stirred for a further 30 minutes. Then, a solution of 6.6 g of sodium hydroxide in 50 ml of water was added and the mixture was heated to reflux for 8 hours. Disappearance of the disubstituted intermediate was confirmed by HPLC, and then, the product was cooled to 40° C., the water layer was removed, and a toluene layer obtained was washed with water and dried with an anhydrous sodium sulfate. The toluene was distilled off at reduced pressure, and the residues obtained were recrystallized from an ethyl acetate to produce the exemplary compound (A-8) at a yield of 88%. $^1$H-NMR, melting point and mass spectra data for the exemplary compound (A-8) will be showed below:

$^1$H-NMR(CDCl$_3$)δ; 3.52 (t, 6H), 3.07 (s, 9H), 1.58 (m, 6H), 1.20–1.33 (m, 54H), 0.88 (t, 9H) melting point: 48° C. MASS: C$_{42}$H$_{84}$N$_6$ Calcd: 672.68. Found: 672.7.

Example 7

<Synthesis of the Exemplary Compound (A-12): Method (1)>

9.2 g of 2,4,6-trichlorotriazine was dissolved into 80 ml of toluene, to which a solution of 40.2 g of 3-n-dodecyloxy-1-propylamine in 20 ml of toluene was added dropwise such that the inner temperature was maintained at 30° C. or below and then, the resulting mixture was stirred for a further 30 minutes. Then, a solution of 6.6 g of sodium hydroxide in 50 ml of water was added and the mixture was heated to reflux for 8 hours. Disappearance of the disubstituted intermediate was confirmed by HPLC, and then, the product was cooled to 50° C., the water layer was removed, and a toluene layer obtained was washed with water and dried with an anhydrous sodium sulfate. The toluene was distilled off at reduced pressure, and the residues obtained were recrystallized from an ethyl acetate to produce the exemplary compound (A-12) at a yield of 90%. $^1$H-NMR, melting point and mass spectra data for the exemplary compound (A-12) will be showed below:

$^1$H-NMR(CDCl$_3$)δ; 4.90–5.06 (br, 3H), 3.36–3.55 (m, 18H), 1.82 (m, 6H), 6H), 1.57 (m, 6H), 1.20–1.40 (m, 54H), 0.89 (t, 3H) melting point: 50° C. MASS: C$_{48}$H$_{96}$N$_6$O$_3$ Calcd: 804.75 Found: 804.8.

Example 8

<Synthesis of the Exemplary Compound (A-17): Method (1)>

18.4 g of 2,4,6-trichlorotriazine was dissolved into 160 ml of toluene, to which a solution of 91.6 g of 4-n-dodecyloxyaniline in 40 ml of toluene was added dropwise such that the inner temperature was maintained at 30° C. or below and then, the resulting mixture was stirred for 60 minutes. Then, a solution of 13.2 g of sodium hydroxide in 100 ml of water was added and the mixture was heated to reflux for 8 hours. Disappearance of the disubstituted intermediate was confirmed by HPLC, and then, the product was cooled to 40° C., the water layer was removed, and a toluene layer obtained was washed with water and dried with an anhydrous sodium sulfate. The toluene was distilled off at reduced pressure, and the residues obtained were recrystallized from an ethyl acetate to produce the exemplary compound (A-17) at a yield of 91%.

Example 9

<Synthesis of the Exemplary Compound (A-19): Method (1)>

9.2 g of 2,4,6-trichlorotriazine was dissolved into 80 ml of toluene, to which a solution of 45.8 g of 3-n-dodecyloxyaniline in 20 ml of toluene was added dropwise such that the inner temperature was maintained at 40° C. or below and then, the resulting mixture was stirred for 60 minutes. Then, a solution of 6.6 g of sodium hydroxide in 50 ml of water was added and the mixture was heated to reflux for 8 hours. Disappearance of the disubstituted intermediate was confirmed by HPLC, and then, the product was cooled to 40° C., the water layer was removed, and a toluene layer obtained was washed with water and dried with an anhydrous sodium sulfate. The toluene was distilled off at reduced pressure, and the residues obtained were recrystallized from an ethyl acetate to produce the exemplary compound (A-19) at a yield of 84%.

Comparative Example 1

<Synthesis of the Exemplary Compound (A-3): Method (1)>(a Methylethylketone was Used as a Solvent)

9.2 g of 2,4,6-trichlorotriazine was dissolved into 80 ml of methylethylketone, to which a solution of 30.6 g of n-dodecylamine in 20 ml of methylethylketone was added dropwise such that the inner temperature was maintained at 30° C. or below and then, the resulting mixture was stirred for 60 minutes. Then, a solution of 6.6 g of sodium hydroxide in 50 ml of water was added and the mixture was heated to reflux for 10 hours. Upon confirming the remaining amount of the disubstituted intermediate by HPLC, it was found that the ratio of the disubstituted intermediate : the trisubstituted porduct is 57:43 at a surface ratio. Then, after the reaction system was further heated to reflux for 8 hours, the surface ratio was then found to be 48:52 for the disubstituted product:the trisubstituted product.

Thereafter, the product was cooled to 60° C., the water layer was removed, and the residue was poured into 300 ml of methanol to precipitate solids. The solids obtained were filtered, dried, and recrystallized from an ethyl acetate. However, when the ratio of the disubstituted intermediate in the product was confirmed by HPLC, the ration of 48:52 for the disubstituted product : the trisubstituted product remained constant at a surface ratio.

Comparative Example 2

<Synthesis of the Exemplary Compound (A-3): Method (1)>(an Ethyl acetate was Used as a Solvent)

9.2 g of 2,4,6-trichlorotriazine was dissolved into 80 ml of ethyl acetate, to which a solution of 30.6 g of n-dodecylamine in 20 ml of ethyl acetate was added dropwise such that the inner temperature was maintained at 30° C. or below and then, the resulting mixture was stirred for 60 minutes. Then, a solution of 6.6 g of sodium hydroxide in 50 ml of water was added and the mixture was heated to reflux for 10 hours. Upon confirming the remaining amount of the disubstituted intermediate by HPLC, it was found that the ratio of the disubstituted intermediate : the trisubstituted porduct is 37:63 at a surface ratio. Then, after the reaction system was further heated to reflux for 8 hours, the surface ratio was then found to be 28:72 for the disubstituted product:the trisubstituted product.

Thereafter, the product was cooled to 60° C., the water layer was removed, and the residue was poured into 300 ml of methanol to precipitate solids. The solids obtained were filtered, dried, and recrystallized from an ethyl acetate. However, when the ratio of the disubstituted intermediate in the product was confirmed by HPLC, the ratio of 28:72 for the disubstituted product: the trisubstituted product remained constant at a surface ratio.

As is clear from Examples 2 to 4 and Comparative Examples 1 and 2 described above, as compared with conventional processes, in the process of the present invention, the reaction proceeds in a shorter time without the disubstituted intermediates remaining, and after-treatment and handling are simpler. Further, according to the invention, the desired products can be obtained with high yield and high purity, and therefore, it is very useful.

In accordance with the present invention, it is possible to provide a simple process for preparing 2,4,6-triaminotriazine. Further, since disubstituted intermediates do not remain, it is possible to provide a preparation process in which separation and/or purification processes are simple, a reaction time is short, yield is high, and mass production with high purity is possible.

All publications, patent applications, and technical standards mentioned in this specification are herein incorporated by reference to the same extent as if each individual publication, patent application, or technical standard was specifically and individually indicated to be incorporated by reference.

What is claimed is:

1. A process for preparing a triazine compound represented by the following formula (1) comprising: reacting 2,4,6-trichlorotriazine, in the presence of a base, with a compound represented by the following formula (2) in a solvent including water and an aromatic hydrocarbon based organic solvent:

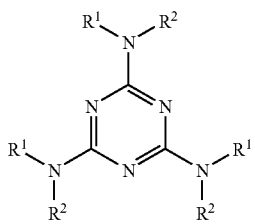

Formula (1)

R¹R²NH   Formula (2):

wherein, $R^1$ represents an alkyl group, an aryl group or a heterocyclic group that may be substituted, and $R^2$ represents a hydrogen atom, or an alkyl group, an aryl group or a heterocyclic group that may be substituted.

2. The process for preparing a triazine compound according to claim 1, wherein in the formula (1), $R^1$ represents an alkyl group and $R^2$ represents a hydrogen atom or an alkyl group.

3. The process for preparing a triazine compound according to claim 1, wherein the aromatic hydrocarbon based organic solvent is toluene.

4. The process for preparing a triazine compound according to claim 2, wherein the aromatic hydrocarbon based organic solvent is toluene.

5. The process for preparing a triazine compound according to claim 1, wherein an inorganic base is used as the base.

6. The process for preparing a triazine compound according to claim 5, wherein a sodium hydroxide, a potassium hydroxide or a combination thereof is used as the inorganic base.

7. The process for preparing a triazine compound according to claim 1, wherein the base is used in an amount of an equimolar amount to an amount 10 times in molar ratio based on the 2,4,6-trichlorotriazine.

8. The process for preparing a triazine compound according to claim 1, wherein the base and water are added after adding the compound represented by the formula (2) to a mixture of 2,4,6-trichlorotriazine and the aromatic hydrocarbon based organic solvent.

9. The process for preparing a triazine compound according to claim 1, wherein after adding a part of the compound represented by the formula (2) to a mixture of 2,4,6-trichlorotriazine and the aromatic hydrocarbon based organic solvent in advance, the remaining compound represented by the formula (2) and the base are simultaneously added.

10. The process for preparing a triazine compound according to claim 1, wherein after adding the base and water to a mixture of 2,4,6-trichlorotriazine and the aromatic hydrocarbon based organic solvent, the compound represented by formula (2) is added thereto.

11. The process for preparing a triazine compound according to claim 1, wherein to a mixture of 2,4,6-trichlorotriazine and the aromatic hydrocarbon based organic solvent, water is added and thereafter, the base and the compound represented by the formula (2) are added.

12. The process for preparing a triazine compound according to claim 1, wherein HCl is neutralized by adding an excess of the compound represented by the formula (2).

13. The process for preparing a triazine compound according to claim 8, wherein an inorganic base is used as the base.

14. The process for preparing a triazine compound according to claim 9, wherein an inorganic base is used as the base.

15. The process for preparing a triazine compound according to claim 10, wherein an inorganic base is used as the base.

16. The process for preparing a triazine compound according to claim 11, wherein an inorganic base is used as the base.

17. The process for preparing a triazine compound according to claim 8, wherein the aromatic hydrocarbon based organic solvent is toluene.

18. The process for preparing a triazine compound according to claim 9, wherein the aromatic hydrocarbon based organic solvent is toluene.

19. The process for preparing a triazine compound according to claim 10, wherein the aromatic hydrocarbon based organic solvent is toluene.

20. The process for preparing a triazine compound according to claim 11, wherein the aromatic hydrocarbon based organic solvent is toluene.

* * * * *